(12) United States Patent
Li et al.

(10) Patent No.: US 10,184,890 B2
(45) Date of Patent: Jan. 22, 2019

(54) GAS ANALYZER WITH LOW OPTICAL NOISE

(71) Applicant: Sharp Kabushiki Kaisha, Osaka (JP)

(72) Inventors: Jing Li, Oxford (GB); Jacob Thomas Barrett, Oxford (GB); Tim Michael Smeeton, Oxford (GB); Valerie Berryman-Bousquet, Oxford (GB)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 15/455,473

(22) Filed: Mar. 10, 2017

(65) Prior Publication Data

US 2018/0259452 A1 Sep. 13, 2018

(51) Int. Cl.
*G01N 21/61* (2006.01)
*G01N 21/05* (2006.01)
*G01N 33/497* (2006.01)
*G01N 21/33* (2006.01)
*G01N 21/03* (2006.01)

(52) U.S. Cl.
CPC ........... *G01N 21/61* (2013.01); *G01N 21/031* (2013.01); *G01N 21/05* (2013.01); *G01N 21/33* (2013.01); *G01N 33/497* (2013.01)

(58) Field of Classification Search
CPC ....... A61B 5/082; A61B 5/083; A61B 5/0833; A61B 5/087; A61B 5/097; A61M 2016/102; A61M 2016/1025; A61M 2016/103; A61M 2016/1035; A61M 2230/43; A61M 2230/432; A61M 2230/435; A61M 2230/437; G01N 21/3504; G01N 21/61; G01N 33/497; G01N 21/031; G01N 21/05
See application file for complete search history.

(56) References Cited

U.S. PATENT DOCUMENTS 5,282,473 A * 2/1994 Braig .................... A61B 5/083
                                                    250/343
5,351,120 A    9/1994 Jurcik et al.
5,570,697 A   11/1996 Walker et al.
8,194,249 B2   6/2012 Haveri et al.
(Continued)

FOREIGN PATENT DOCUMENTS

CN    104251841       12/2014
CN    105259114 A      1/2016
(Continued)

*Primary Examiner* — Violeta A Prieto
(74) *Attorney, Agent, or Firm* — Renner, Otto, Boisselle & Sklar, LLP

(57) ABSTRACT

A gas analyzer and related methods are for measuring a concentration of a component of a gas mixture. The gas analyzer includes a gas cell defining an overall volume for housing the gas mixture, a gas inlet and a gas outlet, a light source that emits a light beam into the gas cell, and a light detector that detects a portion of the light of the light beam that has propagated through the gas mixture, the concentration of the component of the gas mixture being determined based on the portion of the light beam detected by the light detector. The gas cell defines an optical volume for travel of the light beam within the gas cell, and the optical volume comprises at least a portion of the overall volume and is configured to suppress turbulent flow of the gas mixture within the optical volume to reduce optical noise generated by the gas mixture.

6 Claims, 6 Drawing Sheets

(56) References Cited

U.S. PATENT DOCUMENTS

| | | |
|---|---|---|
| 8,399,837 B2 | 3/2013 | Robbins et al. |
| 2004/0137637 A1 | 7/2004 | Wang et al. |
| 2008/0110233 A1* | 5/2008 | Tanaka .................... H01L 22/26 |
| | | 73/1.06 |
| 2010/0208268 A1* | 8/2010 | Haveri ................... G01N 21/05 |
| | | 356/437 |
| 2011/0235042 A1* | 9/2011 | Martin ............... G01N 21/0303 |
| | | 356/437 |
| 2011/0314897 A1* | 12/2011 | Schellekens ....... G01N 29/2406 |
| | | 73/23.3 |
| 2012/0099105 A1* | 4/2012 | Vize .................... G01N 15/0255 |
| | | 356/336 |
| 2015/0276589 A1* | 10/2015 | Wagner ................. G01N 21/39 |
| | | 356/440 |
| 2016/0054294 A1 | 2/2016 | Rihani et al. |
| 2018/0186461 A1* | 7/2018 | Haynes ................. B64D 25/14 |

FOREIGN PATENT DOCUMENTS

| | | |
|---|---|---|
| CN | 205157417 U | 4/2016 |
| WO | WO 2011117572 A1 | 9/2011 |
| WO | WO 2015019650 A1 | 2/2015 |

\* cited by examiner

GAS ANALYZER WITH LOW OPTICAL NOISE

TECHNICAL FIELD

This invention relates to structures for optical-based gas analyzers which have the advantage of small optical noise. It is particularly applicable to real-time breath analyzers for health monitoring and medical applications.

BACKGROUND ART

Human breath contains a variety of volatile organic compounds (VOCs), also known as biomarkers. The concentration of specific biomarkers can be directly linked to a particular disease or health issue. One of the best known and well-studied biomarkers is acetone. Under normal circumstances, our body relies on glucose to provide energy. However, in the condition of glucose depletion, for example due to diet or exercise or having untreated diabetes, the body switches to fat-burning as source of energy and acetone is released into breath during this process. For healthy people with normal diet and activities, the typical breath acetone concentration is below 1 part per million (ppm). Elevated acetone concentration above 1 ppm is a sign for Type 1 or Type 2 diabetes or suggests burning of body fat.

Compared to other diagnosis methods, breath analysis is non-invasive, pain-free, cost effective and easily repeatable. Breath analysis is therefore a very powerful tool for clinical diagnosis or personal health monitoring.

Conventional breath analysis is conducted using gas chromatography with detection methods such as flame ionisation, ion mobility spectrometer and mass spectrometer. These instruments are expensive, bulky and require skilled operators, and thus can only be used in a lab. Other breath analyzers include optical sensors, semiconductor sensors and chemical sensors. Both semiconductor sensors and chemical sensors suffer from low sensitivity and absorption interferences from other VOCs present in both air and breath. Optical sensors can be based on absorption, fluorescence or photoacoustic effects. They are typically more specific and offer higher sensitivity.

The typical concentrations of VOCs in breath are very low, normally in the range of parts per billion (ppb) to ppm. For a breath analyzer based on optical absorption to detect such a small concentration, a long optical path length of the light through the breath is generally necessary. At the same time, it is preferable for a breath analyzer to be compact and portable. Therefore, a compact multipass absorption cell provides a good solution. Furthermore, as VOC concentration in different stages of a breath may vary (e.g. a variation between the start of exhalation and end of exhalation of a breath) and can sometimes provide important medical information, there is a need for a breath analyzer to be able to do real-time measurement.

Traditional multipass absorption cells, such as the Pfund cell, White cell, Herriot cell and circular multipass cell, work by using focusing mirrors to restrict the beam to a predefined space along a controlled path until the beam exits the cells. Since the beam must travel along a controlled path, these cells only work well with well collimated and narrow beam such as lasers.

U.S. Pat. No. 5,570,697A to Walker et al. (1996) describes a multipass cell based on light being reflected between multiple retroreflectors and/or prisms. Again, due to the requirement for controlled beam path, this cell only works for laser beams.

Long optical pathlengths can also be achieved from resonant cavity, such as in cavity ring-down spectroscopy (CRDS) and cavity enhanced absorption spectroscopy (CEAS). Examples include U.S. Pat. No. 8,399,837B2 (Robbins et al., published Mar. 19, 2013), US20040137637A1 (Wang et al., published Jul. 15, 2004), CN105259114A (Li, published Jan. 20, 2016), CN104251841A (Wang et al., published Dec. 31, 2014), and CN205157417U (Suzhou, published Apr. 13, 2016).

Patent Publication WO2015019650A1 to Shioni et al. (2013) describes a breath analyzer based on a double-pass absorption cell.

Patent Publication WO2011117572A1 to Hancock et al. (2010) teaches use of a broadband near infra-red (NIR) light source for breath acetone detection using a resonant optical cavity.

Patent Publication US20040137637A1 to Wang et al. (2003) teaches use of an ultraviolet (UV) light source for breath acetone detection using a resonant optical cavity.

Patent Publication US20160054294A1 to Rihani et al. (2014) presents a gas sensor using one or more UV light emitting diodes (LEDs), especially for measuring acetone in breath.

Use of flow straighteners (honeycombs) for generation of laminar flow is well known, for example in U.S. Pat. No. 8,421,979 to Josephus et al. (1995). The cross-section shapes of these "honeycombs" may be of square, circular and regular hexagonal cells.

U.S. Pat. No. 5,351,120A to Jurcik et al. (1993) presents a conically-shaped spectroscopic sample cell design to reduce gas vortices with the aim of purging the cell more efficiently for accurate measurement of trace impurities.

U.S. Pat. No. 8,194,249B2 to Haveri et al. (2009) proposes a gas cell design to maintain constant and laminar flow throughout and to reduce dead space during gas flow, thereby improving the response time of the analyzer.

SUMMARY OF INVENTION

This invention provides for apparatuses and methods to reduce optical noise in gas analyzers. The present invention is suitable to determine gas concentrations in a gas mixture with high accuracy and fast time response. The present invention is particularly applicable to compact real-time breath acetone analyzers based on UV LEDs for diabetes diagnosis, ketoacidosis diagnosis, fat burning monitoring and weight loss management.

In an aspect of the invention, the measured gas is acetone in exhaled breath. UV LEDs with central wavelengths in the range of 230 nm to 320 nm are used as light sources, and the fraction of the UV light transmitted through the measured gas is used to determine the acetone concentration.

In an aspect of the invention, at least one internal surface of the gas cell is offset from the edge of the "optical volume"—a volume occupied by the light beam and where sensing takes place (i.e. the volume occupied by light which subsequently is incident on a light detector). Turbulence has a potential to occur adjacent to a surface where gas is forced to change flow directions and/or dragging effects occur. If a surface is offset by a distance (for example by a distance of at least 0.5 mm) from the "optical volume", optical noise is advantageously reduced, for example because the "turbulence zone" near the surface is isolated from the "optical volume".

In an aspect of the invention, the gas cell may include a region outside the "optical volume" such that turbulence associated with gas mixing at the gas inlets and gas outlets is outside the "optical volume". This may also reduce optical noise.

In an aspect of the invention, the gas inlet may include one or more active or passive flow controllers so that gas flowing into the "optical volume" has a flow rate smaller than a threshold that marks the transition from laminar flow to turbulent flow. As a result, laminar flow may be maintained in the "optical volume" and optical noise may be reduced.

In an aspect of the invention, an apparatus may include a cell configuration and an associated detection method which contains static gas in the "optical volume" of the cell during measurement while still allowing a continuous flow of gas into the apparatus. The apparatus may include a bypass line for the gas. The apparatus may also contain at least one valve to open and close the bypass line to allow and prevent gas flowing into the "optical volume" of the cell at a different stage of a measurement. Measurement is carried out on static gas and therefore optical noise may be reduced.

This invention provides many advantages which are not suggested from the prior art. The present invention provides solutions to reduce optical noise in gas analyzers, especially those based on compact multipass absorption cells and using LEDs as light sources. The present invention may be useful for making real-time breath analyzers with high measurement precision.

DESCRIPTION OF REFERENCE NUMERALS

Figure 1A:
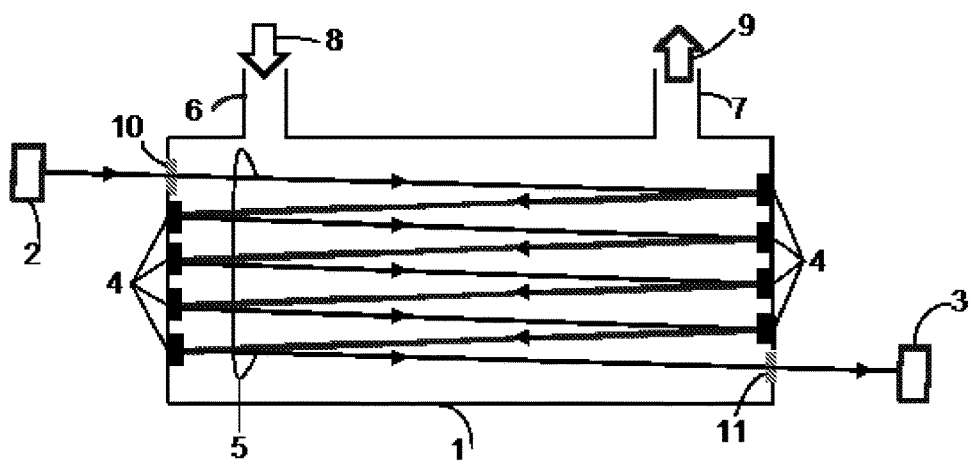
FIG. 1(a), FIG. 1(b) and FIG. 1(c). Schematic of an absorption-based gas analyzer.

1: Gas cell
2: Light source
3: Light detector
4: Mirrors
5: Light beam
6: Inlet
7: Outlet
8: Gas flow in direction
9: Gas flow out direction
10: First window
11: Second window
12: Pre-mixing zone
13: Flow straighter
14: Internal surface
15: A second line
16: Flow controller
17: A length
18: A width
19: Gas flow out direction
20: A central island
21: A volume
22: Window
24: Bypass line
30: Static gas
31: Turbulent gas flow
32: Laminar gas flow
33: Turbulent gas flow
34: Turbulent gas flow
35: Threshold flow rate
41: Gas cell
42: Gas input
43: A first path leading to gas cell
44: Bypass path
45: Gas output
46: A reference gas channel
47: A measurement gas channel
48: Gas cell inlet
49: Gas cell outlet
50: Input valve
51: Output valve
52: First channel valve
53: Second channel valve
54: Filter
60: Cross section of beam 5
61: Volume of beam 5
62: First outline of 61
63: Second outline of 61

DETAILED DESCRIPTION OF INVENTION

This invention provides methods to reduce optical noise in gas analyzers, for example gas analyzers based on optical absorption. The absorption of light by a sample is governed by the empirical Beer-Lambert law:

$$\frac{I_1}{I_0} = \exp(-\alpha(\lambda)L)$$

where $I_0$ and $I_1$ are incident and transmitted intensity respectively; $\lambda$ is a wavelength; $\alpha(\lambda)$ is a wavelength-dependent absorption coefficient; and L is an optical path length of the light through the sample. If the sample contains more than one absorbing gas (specifically, N absorbing gases), the overall absorption coefficient may be calculated by:

$$\alpha(\lambda) = \sum_{i=1 \; to \; N} \sigma_i(\lambda) n_i$$

where $\sigma_i(\lambda)$ and $n_i$ are wavelength-dependent absorption cross-section and concentration respectively, of the $i^{th}$ component.

Figure 1B:
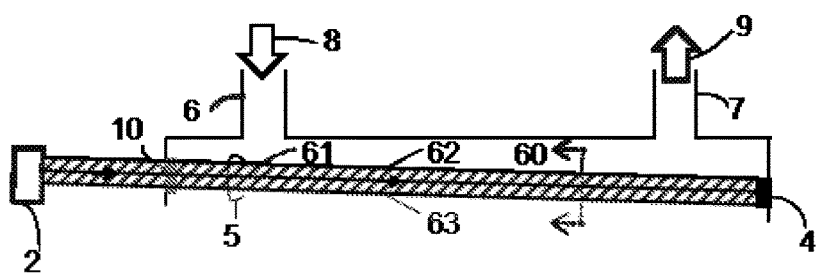
Figure 1C:

The schematic of a basic absorption-based gas analyzer according to the present invention is illustrated in FIG. 1(a). In general, the gas analyzer contains at least one gas cell 1 defining an overall volume for housing a gas mixture, at least one light source 2 emitting a light beam 5 into the gas cell and at least one light detector 3 that detects light of the light beam that has propagated through the gas mixture within the gas cell. Light beam 5 is represented by straight lines in FIG. 1(a) to aid visualisation. However, light beam 5 may occupy a volume 61 and have any cross section 60, as illustrated in FIG. 1(b) and FIG. 1(c), and said cross section 60 may vary along the propagation direction. FIG. 1(b) shows a reproduction of a portion of FIG. 1(a). FIG. 1(c) shows the cross section 60 from FIG. 1(b). Cross section 60 is represented by a circle in FIG. 1(c), but it may have any shape. The outlines of volume 61 are represented by two straight lines 62 and 63 in FIG. 1(b), but 62 and 63 may not be straight lines and may not be parallel to each other. The concentration of the component of the gas mixture (e.g., acetone) may be determined based on the portion of the light beam that is detected by the light detector.

The gas analyzer may contain one or more mirrors 4 to reflect the light beam 5 back and forth in the cell to increase the optical path length of the light through the gas occupying the gas cell. A volume occupied by the light beam 5 is defined as the "optical volume". The "optical volume" is therefore at least a portion of the overall volume defined by the gas cell for housing the gas mixture. The gas cell has at least one inlet 6 and at least one outlet 7 to introduce a gas sample in and out of the cell, as illustrated by arrows 8 and 9 respectively. In an example, a reference gas is first injected into gas cell 1 through inlet 6, and the transmitted light intensity is measured by light detector 3. A breath sample is then injected into gas cell 1 through inlet 6, and transmitted light intensity is again measured by light detector 3. The difference in transmitted light intensity for reference gas and breath sample is defined as the "absorption signal". The absorption signal is due to differences in the absorption and scattering of light with the wavelength emitted by light source 2 by substances that exist in the breath and the reference gas. The "absorption signal" may then be used to calculate the concentration of one or more of the above-mentioned substances in breath.

In one aspect of the invention, the at least one light source 2 includes one or more light emitting diodes (LEDs). They are usually less expensive, consume less energy and are more compact than lasers, and thus are effective light sources for portable and affordable optical sensors.

In one aspect of the invention, the gas to be measured is acetone in human breath. As acetone has a strong absorption band in the UV wavelength range between 230 nm and 320 nm, UV LEDs may be used in a breath acetone analyzer. Accordingly, each LED may have a central wavelength in a range between 230 nm and 320 nm, and a bandwidth of less than 50 nm. In this disclosure the bandwidth of the LED is defined as the full width at half maximum (FWHM) of the spectrum of the LED light. The central wavelength is the wavelength for which the light emitted by the LED has the highest intensity. One significant challenge in producing an accurate breath acetone analyzer is to deal with gases other than acetone that absorb at the same wavelength, an effect known as "cross-sensitivity" or "interference". In one aspect of the invention, the at least one light source 2 includes one or more UV LEDs emitting light with more than one wavelength to mitigate this problem by analysing the absorption of light by the gas mixture at more than one wavelength. By operating using UV wavelengths, a breath analyzer further benefits from very small or zero absorption by water molecules, which is one of the most significant interference substances in breath analyzers at other wavelengths, such as using near infrared.

The typical concentration of biomarkers in breath is in the range of ppb to ppm, and therefore breath analyzers must have high sensitivity. For this purpose, multipass absorption cells may be used, which provide long optical pathlength for sensitivity enhancement while still maintaining compactness of the device. Besides high sensitivity, it is also important for a breath analyzer to have fast time response and be able to conduct real-time measurement. Not only does this deliver better user experience, but also provides information useful for medical diagnosis as the concentration of VOCs in different stages of a breath may change.

Figure 2:
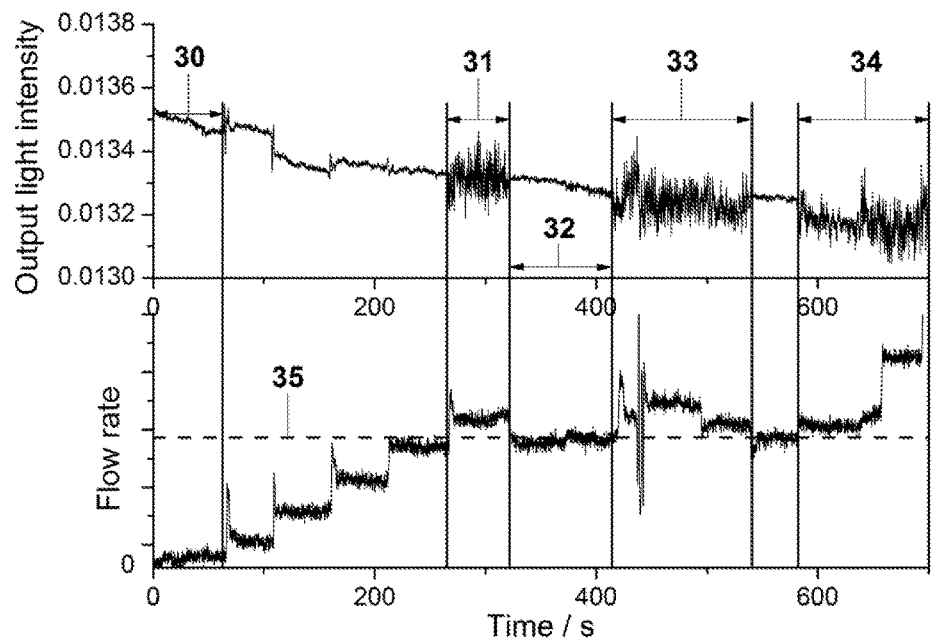
FIG. 2. Experimental data showing noise in transmitted light intensity caused by turbulence when gas flow is increased above a threshold.

The inventors also have discovered a problem that has significant effects on the precision of the breath analyzer. As gas flows through a gas cell, for example as a user exhales directly into the cell, there may be fluctuations in the light intensity measured by the light detector which are large relative to the "absorption signal" that needs to be measured for this application (e.g. the "absorption signal" corresponding to absorption of light by ~ppm concentrations of acetone). FIG. 2 shows the light intensity measured by light detector 3 at different gas flow rates using a gas cell 1 as illustrated in FIG. 1, where the light beam 5 has a peak wavelength of approximately 285 nm and where the total pathlength of light beam 5 through the gas (i.e. the mean distance the light beam 5 propagates between the first window 10 and second window 11 before being incident on the light detector 3) is 94 cm. As can be seen in FIG. 2, when static gas is measured (0-60 s, reference numeral 30), the optical noise, defined as the difference between the minimum measured light intensity and the maximum measured light intensity, is small. The optical noise is determined after the measured light intensity is compensated for slowly-varying changes ("drift"); for the data in FIG. 2, this compensation may be a linear least-squares fit through the data (output light intensity vs time) measured for each gas flow rate. As the gas flow rate is gradually increased in a stepwise fashion, large optical noise with an amplitude of similar magnitude to ~1 ppm of acetone "absorption signal" occurs above a certain threshold flow rate 35 (265-320 s, reference numeral 31). The large noise is not present when the flow rate is reduced below the threshold flow rate 35 (320-410 s, reference numeral 32). The large optical noise has been repeated three times as marked by reference numerals 31, 33 and 34 in FIG. 2 which indicate turbulent flow, and the value of the threshold flow rate 35 remains the same, which suggests said value may be intrinsic to the gas cell for gas of a given temperature. The optical noise may be caused by changing of local refractive index of the gas in the presence of turbulent flow which leads to scattering of light, a phenomenon referred to herein as "turbulent scattering". The presence of this noise only above a threshold flow rate is also consistent with a transition between laminar flow, as indicated with reference numeral 32, and turbulent flow of the gas in the gas cell.

Through this discovery, the inventors have identified a unique new problem to solve to provide an effective breath analyzer. First, a compact cell using LEDs as light sources presents a new challenge over prior art. Because an LED beam is wider and more divergent than a laser beam, the "optical volume" is larger. The "optical volume" as a fraction of the overall volume of the cell is also larger, which means that the gas analyzer is more prone to turbulent scattering. Secondly, UV wavelengths may present new challenges because of the greater sensitivity to turbulent gas flow for short wavelengths. Additionally, a reasonably high flow rate is required to refresh the cell quickly and efficiently for real-time breath measurement. For example, a gas cell may have a total volume of 200 $cm^3$ and may need to be refreshed in less than 5 s for real-time breath measurement, so a flow rate of higher than 40 $cm^3/s$ would be required. Fast gas flow and good gas mixing in a small cell without turbulence is extremely challenging.

The turbulent scattering in an optical analyzer is an unexpected problem which has not been reported in the prior art. Turbulent scattering is especially a problem for a breath analyzer with a compact multipass absorption cell and using UV LEDs as light sources. This invention provides solutions to this problem by configuring the optical volume in a manner that suppresses turbulent flow of the gas mixture within the "optical volume", thereby reducing the optical noise.

Generally, therefore, an aspect of the invention is an enhanced gas analyzer for measuring a concentration of a component of a gas mixture. In exemplary embodiments, the gas analyzer may include: a gas cell defining an overall volume for housing the gas mixture; a gas inlet through which the gas mixture is introduced into the gas cell, and a gas outlet through which the gas mixture is exhausted from the gas cell; a light source that emits a light beam into the gas cell; and a light detector that detects a portion of the light of the light beam that has propagated through the gas mixture in the gas cell, the concentration of the component of the gas mixture being determined based on the portion of the light of the light beam that is detected by the light detector. The gas cell defines an "optical volume" for travel of the light beam within the gas cell, and the "optical volume" comprises at least a portion of the overall volume and is configured to suppress turbulent flow of the gas mixture within the "optical volume" to reduce optical noise generated by the gas mixture. Various ways of configuring the "optical volume" within the gas cell to reduce optical noise are illustrated in the examples below.

The present invention provides accurate measurement of acetone concentration in breath. In an aspect of the invention, the breath analyzer includes a gas cell 1 for receiving a gas mixture, multiple mirrors 4 for creating multiple passes of light in the cell, at least one light source 2 that emits a light beam 5 into the gas cell 1, and at least one light detector 3 that detects a portion of the light from the light source 2 that has propagated through the gas mixture, as illustrated in FIG. 1. The at least one light source 2 may include one or more LEDs, each having a central wavelength between 230 nm and 320 nm and a bandwidth of less than 50 nm. The device may be used to measure acetone concentration in exhaled breath, which may be indicative of fat-burning, diabetes or other health conditions. The gas cell 1 may have at least one gas inlet 6 through which the gas mixture is introduced into the gas cell, and at least one gas outlet 7 through which the gas mixture is exhausted from the gas cell. At least one of the gas inlet(s) 6 and/or at least one of the gas outlet(s) 7 is configured such that gas flowing through the "optical volume" does not cause significant optical noise by resultantly configuring the "optical volume" to suppress turbulent flow of the gas mixture within the "optical volume". Generally, in exemplary embodiments the "optical volume" may be configured as a portion of the overall volume within the gas cell that is less than the entire overall volume defined by the gas cell.

In another aspect of the invention, at least one internal surface of the gas cell is offset from an outer edge of the "optical volume". Turbulence has a potential to occur adjacent to a surface where gas is forced to change flow directions and/or dragging effects occur. If a surface is offset by a distance (for example by a distance of at least 0.5 mm) from the "optical volume", optical noise is advantageously reduced, for example because the "turbulence zone" near the surface is isolated from the "optical volume".

In another aspect of the invention, the gas cell may include a turbulent mixing region outside the "optical volume" such that turbulence associated with gas mixing at the gas inlets and gas outlets is outside the "optical volume". This may also reduce optical noise.

In another aspect of the invention, the gas inlet may include one or more active or passive flow controllers so that gas flowing into the "optical volume" has a rate smaller than a threshold flow rate that marks the transition from laminar flow to turbulent flow. As a result, laminar flow may be maintained in the "optical volume" and optical noise may be reduced.

In an aspect of the invention, an apparatus may include a cell configuration and an associated detection method which contains static gas in the "optical volume" of the cell during measurement while still allowing a continuous flow of gas into the apparatus. The apparatus may include a bypass line for the gas. The apparatus may also contain at least one valve to open and close the bypass line to allow and prevent gas flowing into the "optical volume" of the cell at a different stage of a measurement. Measurement is carried out on static gas and therefore turbulent scattering may be strongly or completely avoided and optical noise may be reduced.

This invention provides solutions to an unexpected problem faced by real-time breath analyzers based on compact multipass absorption cells and using LEDs as light sources. By eliminating the effects of turbulent scattering on the optical signal, the signal to noise ratio of the analyzer may be improved; and real-time breath measurement may be conducted while users exhale continuously.

Furthermore, although the invention has been introduced mostly in the context of a breath analyzer, it may be generally applied to other gas sensors based on optical absorption in which optical noise can reduce performance.

EXAMPLE 1

Figure 3:
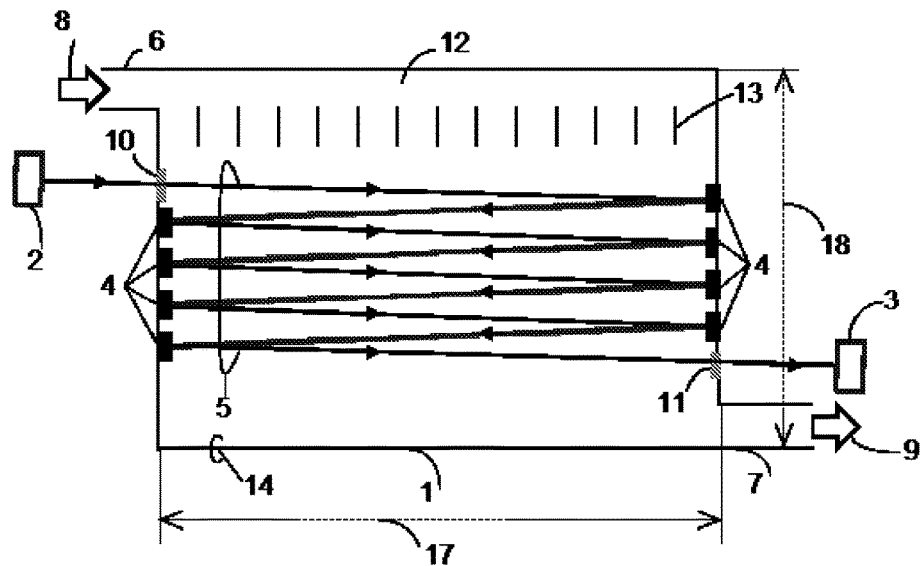
FIG. 3. First example of a gas cell configuration.

A first example of a gas cell configuration for reduction of optical noise is illustrated in FIG. 3. At least one internal surface of the gas cell is offset from the outer edge of the "optical volume". For better optical noise reduction, optionally, the gas cell may also include a region outside the "optical volume" such that turbulence associated with gas mixing and/or inlet and/or outlet flow is outside the "optical volume". In this example, the gas cell may have a flow straightener located between the inner surface of the gas cell and the outer edge of the optical volume on an inlet side of the gas cell relative to the "optical volume".

The gas cell 1 is a multipass absorption cell. Light emitted from light source 2 enters the cell through a first window 10. There may be at least one mirror 4 to reflect the light beam 5 back and forth in the cell through the sample gas. Light beam 5 then leaves the cell through a second window 11 and is then detected by a light detector 3. The "optical volume" is defined by the volume in the cell probed by light beam 5 (i.e. the volume of the light beam which is subsequently incident on the light detector 3). The cell has at least one gas inlet 6 and at least one gas outlet 7 to introduce gas in and out of the cell, as illustrated by arrows 8 and 9 respectively. Both the inlet(s) 6 and outlet(s) 7 are designed such that little or no light can pass through them but gas can. Optionally, the gas cell may also have a pre-mixing zone 12 which is outside of the "optical volume". Gas is first injected into the pre-mixing zone 12 and may then pass through an optional flow straightener 13 before the gas enters the "optical volume". The cross-section shapes of the flow straightener may, for example, be of approximately square, circular or regular hexagonal cells. Low turbulence or laminar flow may be generated by the flow straightener 13 before the gas enters the "optical volume". The gas cell 1 may have a length 17 and a width 18 between 1 cm and 20 cm and a volume in the range of 1 cm$^3$ to 2000 cm$^3$. Preferably, the gas cell 1 has a length and width in the range of 2 cm to 10 cm and a volume in the range of 20 cm$^3$ and 200 cm$^3$. At least one internal surface 14 of the gas cell is offset from the edge of the "optical volume". The distance between internal surface 14 and the "optical volume" of light beam 5 may be larger than 0.5 mm and less than 20 cm. Preferably the distance is at least 1 mm and less than 5 mm.

In an exemplary embodiment, this absorption cell may be used in a breath analyzer to measure acetone concentration in exhaled breath. In this application, the light source may be one or more UV LEDs, each having a central wavelength between 230 nm and 320 nm. A reference gas is first injected into the cell 1 through gas inlet 6 and the transmitted intensity is measured by light detector 3. Breath is then injected into the cell 1, for example via direct exhalation by a user, through gas inlet 6 and the transmitted intensity is measured again. Acetone concentration is calculated based on the difference between the two transmitted intensities. The optical noise has value no bigger than an "absorption signal" caused by 1 ppm of acetone, and preferably no bigger than the "absorption signal" caused by 0.5 ppm of acetone.

EXAMPLE 2

Figure 4:
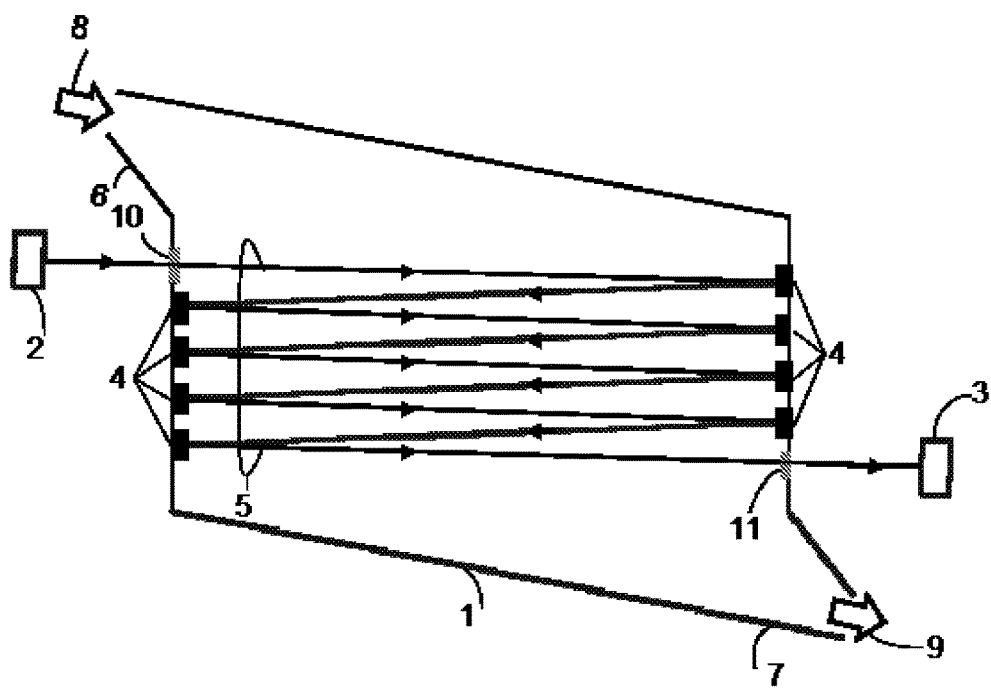
FIG. 4. Second example of a gas cell configuration.

A second example of a gas cell configuration for reduction of turbulence-induced optical noise is shown in FIG. 4. Similar to the cell shown in FIG. 3, this gas cell 1 includes at least one light source 2, at least one light detector 3, optionally at least one mirror 4, at least one gas inlet 6 and at least one gas outlet 7. The "optical volume" is defined as the volume probed by light beam 5 (i.e. the volume of the light beam which is subsequently incident on the light detector 3). The at least one gas inlet 6 has a tapered shape such that the cross-sectional area of the gas inlet perpendicular to the direction of gas flow generally increases along the direction of gas flow towards the "optical volume". Optionally the cross-sectional area of the gas inlet increases continuously along the direction of gas flow towards the "optical volume". Optionally, the cross-sectional area of the gas inlet increases to a maximum value equal to or larger than the area of the intersection between the "optical volume "and the gas flowing into the "optical volume". The at least one gas outlet 7 has a tapered shape such that the cross-sectional area of the gas outlet perpendicular to the direction of gas flow decreases along the direction of gas flow away from the "optical volume". Optionally the cross-sectional area of the gas outlet decreases continuously to a minimum value along the direction of gas flow away from the "optical volume". Optionally, the maximum cross-sectional area of the gas outlet has a value equal to or larger than the area of the intersection between the "optical volume "and the gas flowing out of the "optical volume". When gas flows through the inlet and outlet upon entering and exiting the gas cell 1, the tapered shape makes sure that the gas flow changes gradually and thus turbulence in the "optical volume" is suppressed while also providing a small volume for the gas cell. The optical noise associated with this cell is low.

EXAMPLE 3

Figure 5A:
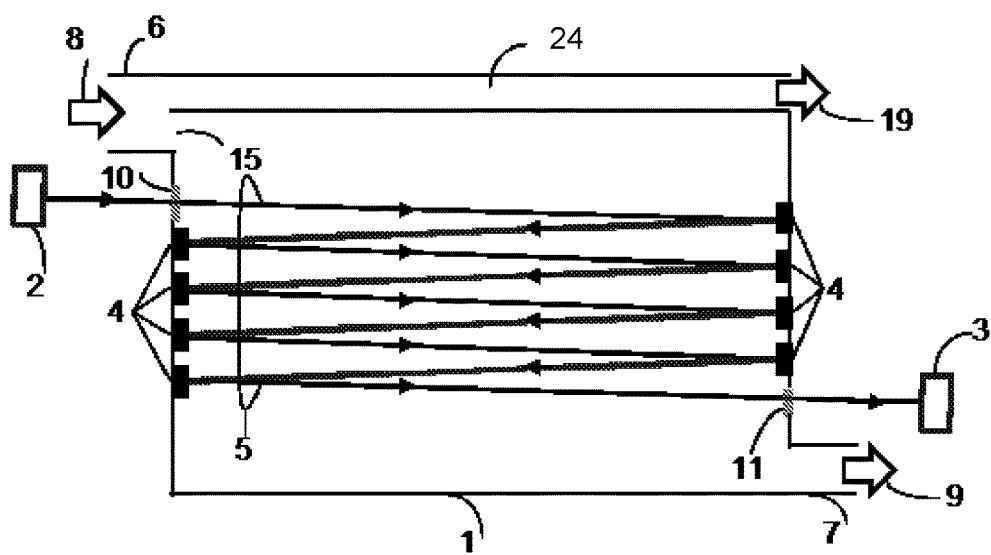
FIG. 5(a) and FIG. 5(b). Third example of a gas cell configuration.
Figure 5B:
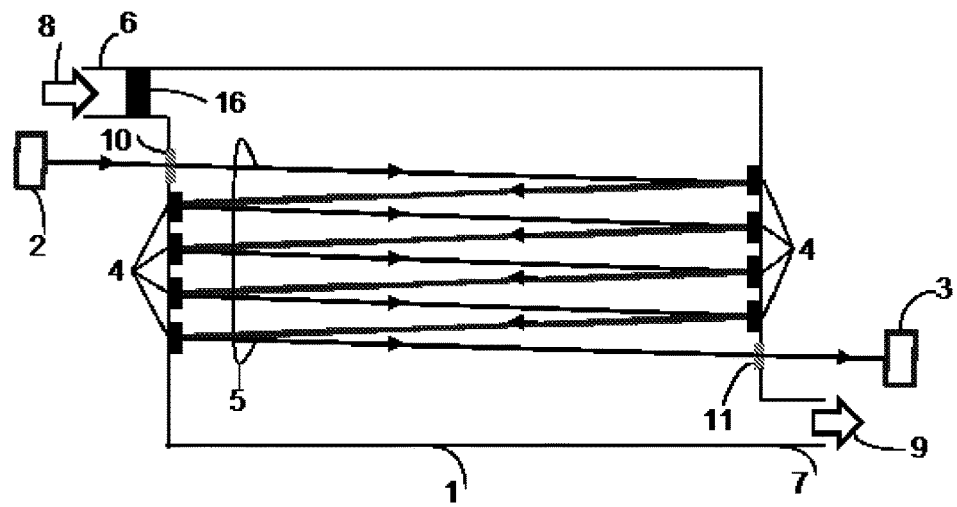

A third example of a gas cell configuration for reduction of turbulence-induced optical noise is shown in FIGS. 5(*a*) and 5(*b*). Similar to the cell shown in FIG. 3, this gas cell 1 includes at least one light source 2, at least one light detector 3, at least one mirror 4, at least one gas inlet 6 and at least one gas outlet 7. The "optical volume" is defined as the volume probed by light beam 5 (i.e. the volume of the light beam which is subsequently incident on the light detector 3). In one aspect, the at least one gas inlet 6 is further divided into two pathways—a bypass line 24 that guides a portion of flow of the gas mixture outside of the "optical volume" as illustrated by arrow 19, and a second line 15 that guides another portion of flow of the gas mixture into the "optical volume", as shown in FIG. 5(*a*). In another aspect, one or more active or passive flow controllers 16 may be used to control the flow rate entering the "optical volume", as shown in FIG. 5(*b*).

The purpose of both the bypass line and flow controllers is to insure that the flow rate entering the "optical volume" does not exceed a turbulent threshold, for example so that laminar flow is always maintained even when the initial flow rate is high, and therefore optical noise may be reduced.

EXAMPLE 4

Figure 6A:
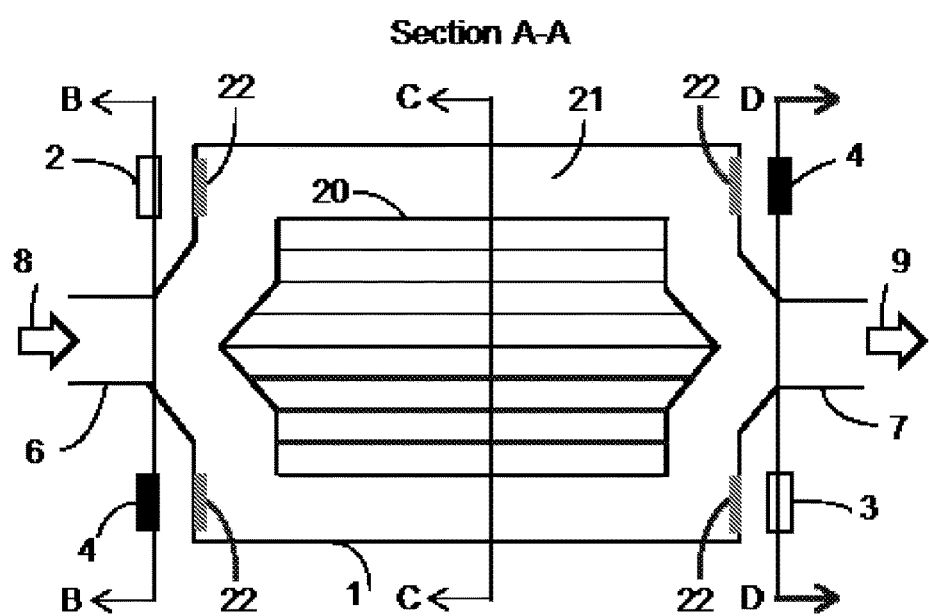
FIG. 6(a) and FIG. 6(b). Fourth example of a gas cell configuration.
Figure 6B:
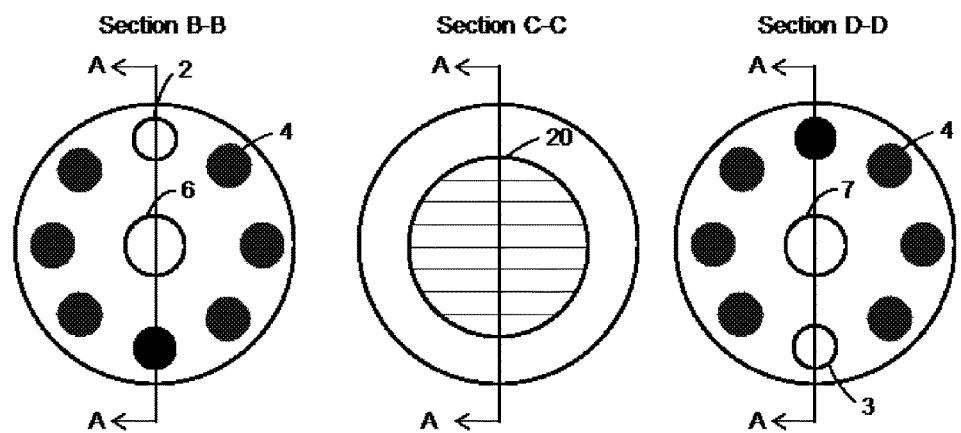

A fourth example of a gas cell configuration for reduction of turbulence-induced optical noise is shown in FIGS. 6(*a*) and 6(*b*). FIG. 6(*a*) shows view at section A-A. This multipass gas cell 1 has a cylindrical shape with a central island 20 located within the overall volume defined by the gas cell. The gas cell 1 includes at least one light source 2, at least one light detector 3, at least one mirror 4, and at least one window 22. The mirrors are arranged in a circular fashion such that light is reflected back and forth in the volume 21 which is between the outer wall of the cell and the central island 20 through windows 22. Accordingly, in this example the "optical volume" is a portion of the overall volume that extends around the island.

The gas cell also contains at least one gas inlet 6 and at least one gas outlet 7 which are preferably located at opposing ends of the cell and near the centre of the circle described by the mirrors 4. The cross-sectional area of the "optical volume" in a plane normal to the predominant flow direction of the gas path throughout the "optical volume" remains substantially constant. The views at sections B-B, C-C and D-D are shown in FIG. 6(*b*), respectively. The substantial constant total cross-sectional area of the gas path through the "optical volume" facilitates uniform and laminar flow throughout the cell and thus reduced optical noise at the detector 3. Although the cross-section is shown as circular here, other cross-sections may similarly provide the advantages of the invention.

EXAMPLE 5

The fifth example is an apparatus including a gas cell 41 that may be used to contain static gas in the "optical volume" during measurement while still allowing a user to exhale continuously into the apparatus.

Figure 7:
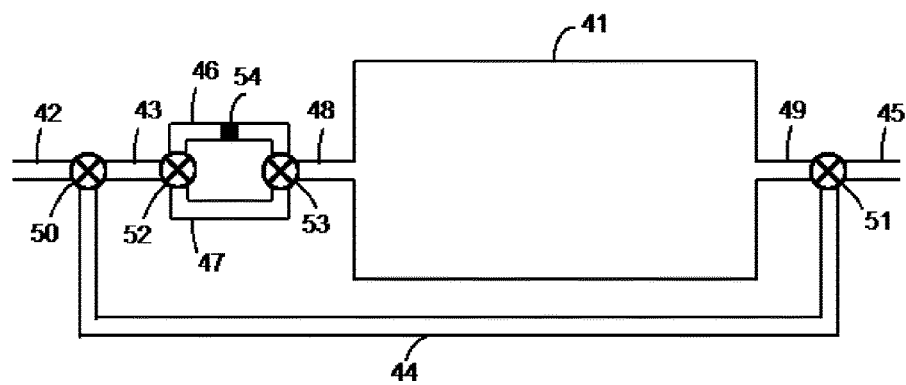
FIG. 7. Fifth example of a gas cell configuration.

As illustrated by FIG. 7, gas is injected from a gas input 42 for receiving an input of the gas mixture. The gas mixture then enters either a first path 43 leading to the gas inlet 48 of the gas cell 41, or a bypass path 44 to avoid entering the gas cell 41 (thereby bypassing the gas cell). Optionally, an input valve 50 is operable to direct flow of the gas mixture to either the first path 43 or the bypass path 44. Optionally, an output valve 51 is operable on the gas cell outlet 49. In a first example, the output valve may be operable to prevent flow of gas into and out of the gas cell outlet 49, thereby sealing the gas in the gas cell 41. In a second example, the output valve may be operable to direct flow of gas to the gas output 45 from either the bypass path 44 or the gas cell outlet 49. In either example, when the output valve 51 prevents flow of gas into and out of the gas cell outlet 49, thereby for example preventing backflow of gas from the gas output 45 into the gas cell 41, the stability of the sensor may be improved. The gas cell 41 defines the optical volume, which comprises at least a portion of the overall volume of the gas cell 41. When the gas mixture is present in the "optical volume", the input valve and the output valve are operable to open the bypass path and seal the gas mixture within the gas cell as a static gas.

In the application of breath acetone analyzer, optionally, path 43 may further divide into two channels 46 and 47. A reference gas channel 46 located between the gas input and the gas inlet to the gas cell may be used to produce the reference gas. Specifically, the reference gas channel may contain at least one filter 54 which removes some or all of the component being measured (e.g., acetone) from the exhaled breath gas mixture to produce the reference gas for introduction into the gas cell. Optionally, the filter 54 may include one or more of molecular sieves and silica gel. A measurement gas channel 47 between the gas input and the gas inlet to the gas cell, and separate from the reference gas channel, may be used to introduce the measurement gas sample, in this case unfiltered breath gas mixture, into the gas cell. A channel valve system is operable to direct the gas mixture into the gas cell via either the reference gas channel or the measurement gas channel. For example, the channel valve system may include a first channel valve 52 and a second channel valve 53 to open and close channels 46 and 47 respectively. Both reference gas and measurement gas enter and leave the gas cell 41 from gas cell inlet 48 and gas cell outlet 49, respectively.

Figure 8:
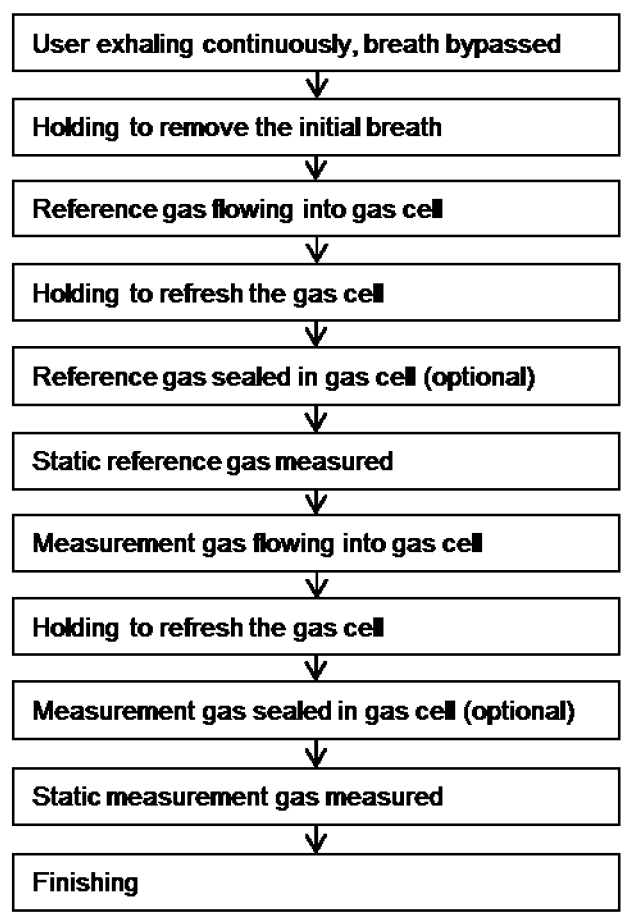
FIG. 8. Flow chart of a detection method associated with the gas cell configuration in FIG. 7.

A detection method associated with breath acetone measurement is illustrated by the flow chart shown in FIG. 8. The detection method may contain some or all of the following steps, and the orders of the steps may be varied as appropriate:

The user exhales continuously into the breath analyser throughout the following steps.

1. By default, valve 50 is configured to open bypass 44, and close path 43 (i.e. 42 flows to 44). The breath is bypassed away from the gas cell 41.
2. Pause for a first period of time.
3. Valve 50 is configured to close bypass 44, and open path 43 (i.e. 42 flows to 43). Valves 52 and 53 are configured to open channel 46 and close channel 47 (i.e. 43 flows to 46, and 46 flows to 48). Acetone in breath is removed by filter 54 and reference gas flows into the gas cell 41 via input 48.
4. Pause for a second period of time during which the breath displaces some or all of the gas previously in the gas cell 41.
5. Valve 50 is configured to open bypass 44, and close path 43 (i.e. 42 flows to 44). Optionally, valve 51 is configured to close output 49. Reference gas is thereby sealed in the gas cell.
6. Take measurement of the static reference gas.
7. Valve 50 is configured to close bypass 44, and open path 43 (i.e. 42 flows to 43). Valves 52 and 53 are configured to close channel 46 and open channel 47 (i.e. 43 flows to 47, and 47 flows to 48). Measurement gas flows into the gas cell 41 via input 48.
8. Pause for a third period of time during which the breath displaces some or all of the gas previously in the gas cell 41.
9. Valve 50 is configured to open bypass 44, and close path 43 (i.e. 42 flows to 44). Optionally, valve 51 is configured to close output 49. Measurement gas is thereby sealed in the gas cell.
10. Take measurement of the static measurement gas.
11. Measurement finishes, and may optionally be repeated.

Alternatively, the detection method may contain some or all of the following steps, and the orders of the steps may be varied as appropriate:

The user exhales continuously into the breath analyser throughout the following steps.

1. By default, valves 50 and 51 are configured to open bypass 44, and close path 43 (i.e. 42 flows to 44) and output 49 (i.e. 44 flows to 45). The breath is bypassed away from the gas cell 41.
2. Pause for a first period of time.
3. Valves 50 and 51 are configured to close bypass 44, and open path 43 (i.e. 42 flows to 43) and open output 49 (i.e. 49 flows to 45). Valves 52 and 53 are configured to open channel 46 and close channel 47 (i.e. 43 flows to 46, and 46 flows to 48). Acetone in breath is removed by filter 54 and reference gas flows into the gas cell 41 via input 48.
4. Pause for a second period of time during which the breath displaces some or all of the gas previously in the gas cell 41.
5. Valves 50 and 51 are configured to open bypass 44, and close path 43 (i.e. 42 flows to 44) and close output 49 (i.e. 51 flows to 45). Reference gas is thereby sealed in the gas cell.
6. Take measurement of the static reference gas.
7. Valves 50 and 51 are configured to close bypass 44, and open path 43 (i.e. 42 flows to 43) and open output 49 (i.e. 49 flows to 45). Valves 52 and 53 are configured to close channel 46 and open channel 47 (i.e. 43 flows to 47, and 47 flows to 48). Measurement gas flows into the gas cell 41 via input 48.
8. Pause for a third period of time during which the breath displaces some or all of the gas previously in the gas cell 41.
9. Valves 50 and 51 are configured to open bypass 44, and close path 43 (i.e. 42 flows to 44) and close output 49 (i.e. 44 flows to 45). Measurement gas is thereby sealed in the gas cell.
10. Take measurement of the static measurement gas.
11. Measurement finishes, and may optionally be repeated.

The configuration of a reference gas channel 46, measurement gas channel 47, filter 52, and optional first channel valve 52 and optional second channel valve 53 to provide filtered and unfiltered gas to the gas cell 1 may be applied in combination with any of the examples 1 to 4, without the use of a bypass path 44 and valve 50.

An aspect of the invention, therefore, is a gas analyzer for measuring a concentration of a component of a gas mixture. In exemplary embodiments, the gas analyzer includes a gas cell defining an overall volume for housing the gas mixture, a gas inlet through which the gas mixture is introduced into the gas cell, and a gas outlet through which the gas mixture is exhausted from the gas cell, a light source that emits a light beam into the gas cell, and a light detector that detects a portion of the light of the light beam that has propagated through the gas mixture in the gas cell, the concentration of the component of the gas mixture being determined based on the portion of the light of the light beam that is detected by the light detector. The gas cell defines an optical volume for travel of the light beam within the gas cell, and the optical volume comprises at least a portion of the overall volume and is configured to suppress turbulent flow of the gas mixture within the optical volume to reduce optical noise generated by the gas mixture. The gas analyzer may include one or more of the following features, either individually or in combination.

In an exemplary embodiment of the gas analyzer, the optical volume is a portion of the overall volume within the gas cell that is less than the entire overall volume.

In an exemplary embodiment of the gas analyzer, the gas cell has an internal surface that is offset from an outer edge of the optical volume.

In an exemplary embodiment of the gas analyzer, an inner surface of the gas cell is spaced apart from a closest outer edge of the optical volume by a distance between 0.5 mm and 20 cm.

In an exemplary embodiment of the gas analyzer, the gas analyzer further includes a flow straightener located between the inner surface of the gas cell and the outer edge of the optical volume on an inlet side of the gas cell relative to the optical volume.

In an exemplary embodiment of the gas analyzer, at least one of the gas inlet or gas outlet has a tapered shape such that at least a portion of a cross-sectional area of the gas inlet perpendicular to a direction of gas flow increases along the direction of gas flow, and/or at least a portion of a cross-sectional area of the gas outlet perpendicular to a direction of gas flow decreases along the direction of gas flow.

In an exemplary embodiment of the gas analyzer, the gas inlet is divided into a bypass line that guides a portion of flow of the gas mixture outside of the optical volume, and a second line that guides another portion of flow of the gas mixture into the optical volume.

In an exemplary embodiment of the gas analyzer, the gas inlet includes a flow controller operable to control a flow rate of the gas mixture entering the optical volume to produce a laminar flow.

In an exemplary embodiment of the gas analyzer, the gas cell includes a turbulent mixing region for the gas mixture that is outside of the optical volume.

In an exemplary embodiment of the gas analyzer, the gas analyzer further includes an island centrally located within the overall volume of the gas cell, and the optical volume comprises a portion of the overall volume that extends around the island, and a cross-sectional area of the optical volume is configured to generate a laminar flow of the gas mixture through the gas cell.

In an exemplary embodiment of the gas analyzer, the gas analyzer further includes a gas input for receiving an input of the gas mixture; a first path for communication of the gas mixture from the gas input to the gas inlet of the gas cell; a bypass path for communication of the gas mixture from the gas input to in a flow path bypassing the gas cell; an input valve operable to direct flow of the gas mixture to either the first path or the bypass path; and an output valve operable to control flow of the gas mixture from the gas cell to the gas outlet; wherein the gas cell defines the optical volume, and when the gas mixture is present in the optical volume, the input valve and the output valve are operable to open the bypass path and seal the gas mixture within the gas cell as a static gas.

In an exemplary embodiment of the gas analyzer, the gas analyzer further includes a reference gas channel between the gas input and the gas inlet to the gas cell, the reference gas channel including a filter to remove some or all of the component of the gas mixture being measured from the gas mixture to produce a reference gas for introduction into the gas cell; a measurement gas channel between the gas input and the gas inlet to the gas cell different from the reference gas channel, for introduction of the gas mixture into the gas cell; and a channel valve system operable to direct the gas mixture into the gas cell via either the reference gas channel or the measurement gas channel.

In an exemplary embodiment of the gas analyzer, the filter is at least one of silica gel and molecular sieve.

In an exemplary embodiment of the gas analyzer, the gas analyzer further includes a plurality of reflectors positioned to create multiple passes of the light beam through the optical volume within the gas cell.

In an exemplary embodiment of the gas analyzer, the light source comprises one or more light emitting diodes (LEDs), with each LED having a central wavelength in a range between 230 nm and 320 nm, and having a bandwidth of less than 50 nm.

Another aspect of the invention is a method of measuring a concentration of a component of a gas mixture. In exemplary embodiments, the measuring method includes steps of: introducing a reference gas as the gas mixture into a gas cell defining an overall volume; emitting a light beam from a light source into the gas cell to propagate through the reference gas within an optical volume for travel of the light beam within the gas cell, the optical volume comprising at least a portion of the overall volume and is configured to suppress turbulent flow of the gas mixture to reduce optical noise generated by the gas mixture within the optical volume; detecting a portion of the light beam from the light source that has propagated through the reference gas in the chamber with a light detector, and determining a first ratio of power of the light emitted from the light source to power of the light detected by the light detector; introducing a measurement gas mixture into the gas cell; emitting a light beam from the light source into the gas cell to propagate through the measurement gas mixture within the optical volume; detecting a portion of the light beam from the light source that has propagated through the measurement gas mixture in the chamber with the light detector, and determining a second ratio of power of the light emitted from the light source to power of the light detected by the light detector; and calculating a concentration of a component of the measurement gas mixture based on the first and second ratios. The measure method may include one or more of the following features, either individually or in combination.

In an exemplary embodiment of the measuring method, the method further includes inputting the gas mixture into a gas input of a gas analyzer including the gas cell; providing a first path in the gas analyzer for communication of the gas mixture from the gas input to a gas inlet of the gas cell; providing a bypass path in the gas analyzer for communication of the gas mixture from the gas input to a gas outlet thereby bypassing the gas cell; operating an input valve to direct flow of the gas mixture to either the first path or the bypass path; and operating an output valve to control flow of the gas mixture from the gas cell to the gas outlet; wherein the gas cell defines the optical volume, and when the gas mixture is present in the optical volume, the input valve and the output valve are operated to open the bypass path and seal the gas mixture within the gas cell as a static gas.

In an exemplary embodiment of the measuring method, the method further includes providing a reference gas channel between the gas input and the gas inlet to the gas cell, the reference gas channel including a filter to remove the component of the gas mixture being measured from the gas mixture to produce the reference gas for introduction into the gas cell; providing a measurement gas channel between the gas input and the gas inlet to the gas cell different from the reference gas channel, for introduction of the measurement gas mixture into the gas cell; introducing the reference gas into the gas cell comprises operating a channel valve system to direct the gas mixture into the gas cell via the reference gas channel to generate the reference gas for introduction into the gas cell; and introducing the measurement gas mixture into the gas cell comprises operating the channel valve system to direct the gas mixture into the gas cell via the measurement gas channel.

In an exemplary embodiment of the measuring method, the gas mixture comprises exhaled breath that is exhaled into the gas input, the method comprising operating the input valve and the output valve to permit exhaling continuously into the gas input while the gas mixture is sealed within the gas cell as the static gas.

In an exemplary embodiment of the measuring method, the component of the measurement gas mixture for which concentration is determined includes acetone.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

INDUSTRIAL APPLICABILITY

This invention can be used for the following applications:
Diabetes Diagnosis and Screening.
Health/Diet Support, Weight Monitoring.
Body fat-burning Monitor.
Prevention of Ketoacidosis.
Insulin Management.
Blood Glucose monitoring and management.

What is claimed is:

1. A gas analyzer for measuring a concentration of a component of a gas mixture, the gas analyzer comprising:
a gas cell defining an overall volume for housing the gas mixture;
a gas inlet through which the gas mixture is introduced into the gas cell, and a gas outlet through which the gas mixture is exhausted from the gas cell;
a light source that emits a light beam into the gas cell; and
a light detector that detects a portion of the light of the light beam that has propagated through the gas mixture in the gas cell;
wherein:
the gas cell defines an optical volume for travel of the light beam within the gas cell, and the optical volume comprises at least a portion of the overall volume and is configured to suppress turbulent flow of the gas mixture within the optical volume to reduce optical noise generated by the gas mixture;
the optical volume is a portion of the overall volume within the gas cell that is less than the entire overall volume;
the gas cell has an internal surface that is offset from an outer edge of the optical volume; and
the gas analyzer further comprises a flow straightener located between the inner surface of the gas cell and the outer edge of the optical volume on an inlet side of the gas cell relative to the optical volume.

2. The gas analyzer of claim 1, wherein an inner surface of the gas cell is spaced apart from a closest outer edge of the optical volume by a distance between 0.5 mm and 20 cm.

3. The gas analyzer of claim 1, further comprising:
a reference gas channel between a gas input and the gas inlet to the gas cell, the reference gas channel including a filter to remove some or all of the component of the gas mixture being measured from the gas mixture to produce a reference gas for introduction into the gas cell;
a measurement gas channel between the gas input and the gas inlet to the gas cell different from the reference gas channel, for introduction of the gas mixture into the gas cell; and
a channel valve system operable to direct the gas mixture into the gas cell via either the reference gas channel or the measurement gas channel.

4. The gas analyzer of claim 3, wherein the filter is at least one of silica gel and molecular sieve.

5. The gas analyzer of claim 1, further comprising a plurality of reflectors positioned to create multiple passes of the light beam through the optical volume within the gas cell.

6. The gas analyzer of claim 1, wherein the light source comprises one or more light emitting diodes (LEDs), with each LED having a central wavelength in a range between 230 nm and 320 nm, and having a bandwidth of less than 50 nm.

* * * * *